(12) United States Patent
Biesel

(10) Patent No.: US 6,964,646 B1
(45) Date of Patent: Nov. 15, 2005

(54) DEVICE AND METHOD FOR AUTOLOGOUS BLOOD TRANSFUSION

(75) Inventor: Wolfgang Biesel, Ottweiler (DE)

(73) Assignee: Fresenius HemoCare GmbH, Bad Homburg (DE)

( * ) Notice: Subject to any disclaimer, the term of this patent is extended or adjusted under 35 U.S.C. 154(b) by 398 days.

(21) Appl. No.: 09/636,123

(22) Filed: Aug. 10, 2000

(30) Foreign Application Priority Data

Aug. 12, 1999 (DE) ............................... 199 38 287

(51) Int. Cl.[7] .................... A61M 5/00; A61M 37/00; C02F 1/38; C02F 9/00; B02D 33/00
(52) U.S. Cl. .................... 604/7; 604/5.01; 604/6.01; 604/6.09; 604/6.15; 210/782; 210/348; 210/295; 210/258; 210/252
(58) Field of Search .............................. 604/4.01, 5.01, 604/5.02, 6.01, 6.03, 6.07, 609, 406, 6.06, 604/7, 6.15, 403, 405, 408, 254–258, 262, 604/317, 319–320; 210/645, 646, 782, 767–777, 210/294–295, 322, 323.1, 342, 348, 359, 210/360.2, 361, 800, 804–805, 787, 252, 210/255, 257.1; 494/36

(56) References Cited

U.S. PATENT DOCUMENTS

| | | | |
|---|---|---|---|
| 4,146,172 A * | 3/1979 | Cullis et al. .................. 494/17 |
| 4,243,531 A | 1/1981 | Crockett et al. | |
| 4,466,888 A * | 8/1984 | Verkaart ...................... 210/232 |
| 4,968,295 A * | 11/1990 | Neumann .................. 604/6.07 |
| 4,976,682 A * | 12/1990 | Lane et al. ................. 604/6.07 |
| 5,417,650 A * | 5/1995 | Gordon ...................... 604/5.04 |
| 5,472,605 A * | 12/1995 | Zuk, Jr. ...................... 210/436 |
| 5,494,592 A * | 2/1996 | Latham et al. .............. 210/805 |
| 5,607,830 A * | 3/1997 | Biesel et al. .................... 435/2 |
| 5,643,193 A * | 7/1997 | Papillon et al. ............ 604/6.07 |
| 5,744,047 A | 4/1998 | Gsell et al. | |
| 5,919,125 A | 7/1999 | Berch | |
| 5,935,092 A * | 8/1999 | Sun et al. .................. 604/6.03 |
| 6,033,561 A * | 3/2000 | Schoendorfer ........... 210/195.1 |
| 6,251,291 B1 * | 6/2001 | Lamphere et al. .......... 210/767 |

FOREIGN PATENT DOCUMENTS

| BE | 1005193 A3 | 5/1993 |
|---|---|---|
| DE | 42 26 974 | 2/1994 |
| DE | 42 27 695 | 10/1999 |
| WO | WO 97/15399 | 5/1997 |
| WO | 99/02269 | 1/1999 |

* cited by examiner

*Primary Examiner*—Patricia Bianco
(74) *Attorney, Agent, or Firm*—Kenyon & Kenyon

(57) ABSTRACT

A device for autologous blood transfusion includes a centrifuge unit with an autotransfusion set rotatably mounted thereto. The autotransfusion set includes a separation unit for concentrating a cell fraction by centrifugation and a tubing system for providing a connection to a blood supply. The tubing system includes a blood supply line leading to the separation unit for supplying blood to be processed and a return line leading away from the separation unit. A filter is integrated into the autotransfusion set in order to eliminate leukocytes and/or tumor cells, thereby yielding greater safety in autotransfusion.

6 Claims, 1 Drawing Sheet

DEVICE AND METHOD FOR AUTOLOGOUS BLOOD TRANSFUSION

FIELD OF THE INVENTION

The present invention relates to a device for autologous blood transfusion having a centrifuge unit with an autotransfusion set mounted thereto. The present invention also relates to a method of autologous blood transfusion.

BACKGROUND OF THE INVENTION

There are various known devices and methods of obtaining concentrates from certain blood components. To obtain a platelet concentrate, for example, blood from a donor in an extracorporeal circulation is centrifuged and separated into its components. An example of a device for carrying out such a method is disclosed in German Patent Application No. 42 27 695.

Platelet concentrates are needed for treating thrombocytopenic patients. Although it is generally sufficient to separate leukocytes by centrifugation, leukocytes, which are capable of causing an immune response, are preferably eliminated in transfusions of foreign blood to prevent undesirable immune system reactions in a patient.

In addition to transfusion of foreign blood, there has been widespread use of intraoperative autotransfusion, where the patient's own blood is collected during the surgery and retransfused back into the patient. The advantage of transfusion of autologous blood is that it prevents the transmission of infectious diseases such as AIDS and hepatitis while also avoiding transfusion reactions due to biological incompatibility and immune system reactions. So-called whole blood transfusion methods, where the collected blood is merely subjected to particle filtration, and plasma separation/washing methods, which supply washed erythrocyte concentrates for reinfusion, are used in the field of intraoperative autotransfusion. An example of a known autologous blood transfusion device is described in International Patent Application No. WO 99/02269.

In transfusion of foreign blood, there is the risk of immune reactions, but immune reactions do not occur with autotransfusion (autologous blood transfusion). On the other hand, the possibility of physiological reactions cannot be ruled out because the leukocytes are traumatized and/or activated in collection. It has been found that tumor cells, which may result from the autologous blood transfusion, may be eliminated by leukocyte depletion filters. U.S. Pat. No. 5,744,047 describes a leukocyte filter which is also used for autologous blood transfusions.

SUMMARY OF THE INVENTION

The object of the present invention is to create a device for autologous transfusion of blood with a centrifuge unit having an autotransfusion set rotatably mounted thereto and an autotransfusion set for such a device so that the safety of autologous transfusion is further increased.

Another object of the invention is to provide an improved method of autologous blood transfusion.

To prevent physiological reactions due to activated or traumatized leukocytes or metastases due to tumor cells, a filter for eliminating leukocytes and/or tumor cells that may cause immune reactions or metastases is integrated into the autotransfusion set. Leukocytes and/or tumor cells are eliminated with the known leukocyte depletion filters which can also bind specific tumor cells in addition to leukocytes. In addition, particulate impurities are eliminated by the leukocyte depletion filters.

Leukocytes and/or tumor cells can be eliminated in principle before or after processing the blood. However, eliminating the leukocytes before processing reduces the quantity of products of leukocyte activation or traumatization of the blood product for transfusion. Therefore, the filter for elimination of leukocytes and/or tumor cells is preferably arranged in the blood supply line leading to the separation unit of the autotransfusion set.

Known autotransfusion sets generally have a collecting tank, also known as a cardio reservoir, arranged in the blood supply line. The filter for eliminating leukocytes and/or tumor cells is preferably arranged in the collecting tank. This is advantageous inasmuch as no separate filter housing is needed. Providing the leukocyte depletion filter in the collecting tank not only eliminates the need to provide a separate filter housing but also prevents the risk of leakage due to additional connecting parts. The filter for eliminating leukocytes and/or tumor cells may be arranged in the collecting tank together with the filter which is preferably generally provided with the known cardio reservoir to remove particulate impurities. To this extent, the manufacturing cost is low.

If the autologous blood is filtered before being collected in the tank, a rapid reinfusion is possible if necessary. However, placing the filter in the blood supply line leading to the patient limits the flow of the cell fraction to be retransfused back into the patient. The filter for eliminating leukocytes and/or tumor cells should have the largest possible filter surface area so that large volumes of blood can be freed of leukocytes and/or tumor cells in a short period of time.

DETAILED DESCRIPTION

Figure 1:
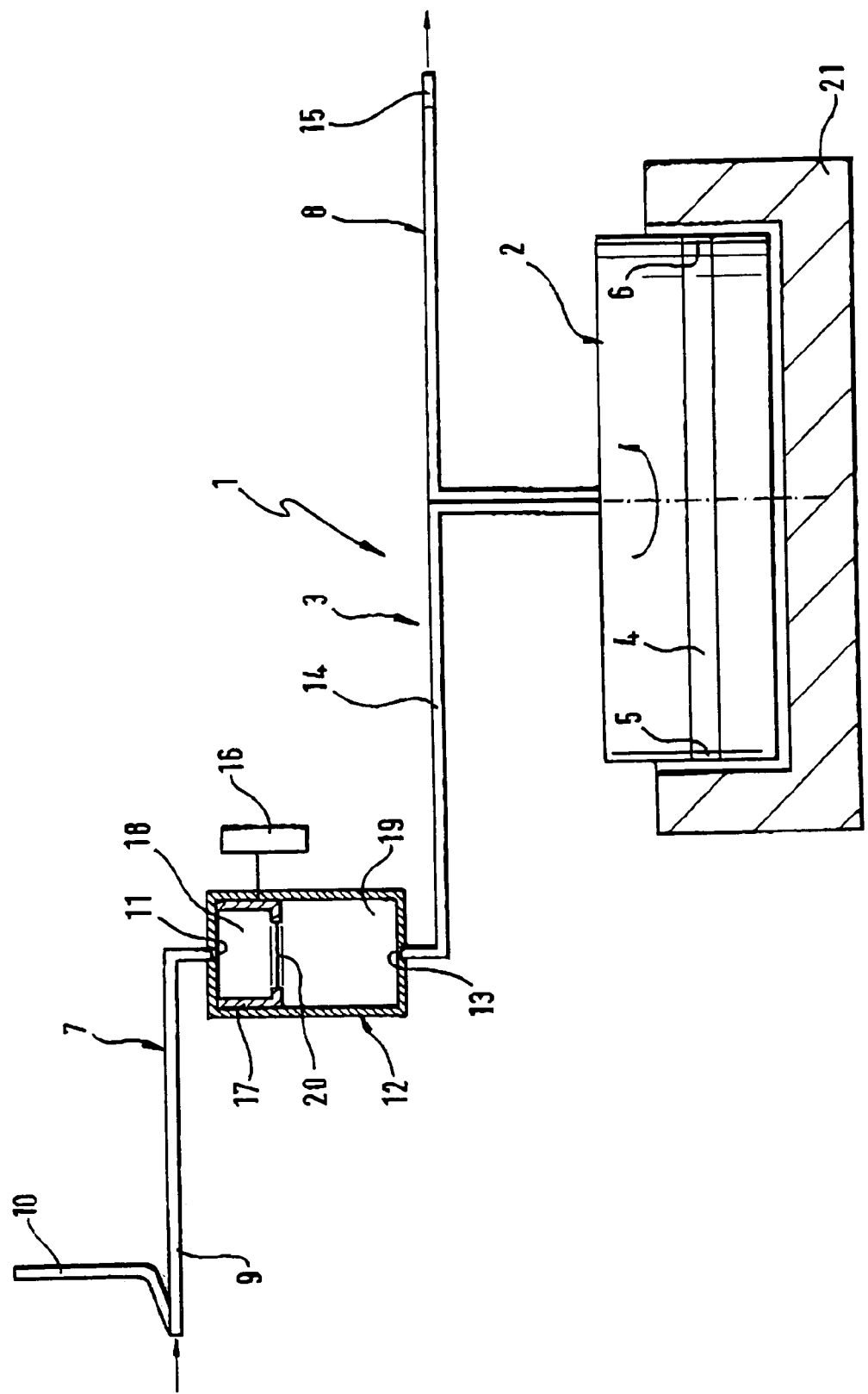
FIG. 1 shows a schematic diagram of the device for autologous blood transfusion together with the autotransfusion set according to the present invention.

FIG. 1 illustrates the components of a device for autologous transfusion of blood together with the autotransfusion set in a simplified diagram. The autotransfusion set, which is designed as a disposable set, is inserted into the device for autologous transfusion. The autotransfusion set 1 comprises a separation unit 2 for concentrating a cell fraction and a tubing system 3 for providing a connection to a patient.

Separation unit 2 is a centrifuge chamber with an annular channel 4 having an inlet 5 for the blood to be processed and an outlet 6 for the concentrated cell fraction, e.g., an erythrocyte concentrate. Such a centrifuge chamber is described in detail in U.S. Pat. No. 5,607,830, for example, which is incorporated herein by reference.

The tubing system 3 of the autotransfusion set comprises a blood supply line 7 for supplying blood removed from the patient, and a blood return line 8 for retransfusion of the blood processed in the separation unit 2.

Blood supply line 7 leads to the inlet 11 of a collecting tank 12 for the collected, anticoagulant-treated blood. A second section 14 of the blood supply line 7 leads from the outlet 13 of collecting tank 12 to the inlet 5 of separation channel 4. The blood return line 8 is connected to the outlet 6 of channel 4 and has at the end a connection 15 to a transfer bag (not shown). The collecting tank 12 is connected to a device 16 for generating a vacuum to draw the blood in. A filter insert 17 inserted into collecting tank 12 has a filter 20 dividing the collecting tank into two chambers to eliminate leukocytes and/or tumor cells. A connection 10 is provided for supplying an anticoagulant.

The device for autologous transfusion of blood has a centrifuge unit 21. The separation unit 2 of the autotransfusion set 1 is positioned in the device for autologous transfusion to provide for the rotation of the separation unit. The patient's blood to be processed flows through the first section 9 of the blood supply line 7 into the first chamber 18 and through filter 20 into the second chamber 19 of the collecting tank 12, where leukocytes and/or tumor cells are retained. Blood from which the leukocytes and/or tumor cells have been removed then flows out of collecting tank 12, through the second section 14 of the blood supply line 7 into the rotating separation unit 2, where a cell fraction such as the erythrocyte fraction is concentrated. The erythrocyte concentrate is then sent to the transfer bag (not shown) through the blood return line 8 for temporary storage and is reinfused back into the patient.

The present invention may be embodied in other specific forms without departing from the spirit or essential attributes thereof and accordingly reference should be made to the appended claims rather than the foregoing specification as indicating the scope of the invention.

What is claimed is:

1. A device for autologous blood transfusion comprising:
   an autotransfusion set including a separation unit for concentrating a cell fraction, a tubing system for providing a connection to a blood supply, a filter means for eliminating at least one of leukocytes and tumor cells, a blood collecting tank having an inlet and an outlet, and a device for generating a vacuum connected to the blood collecting tank, the tubing system including a blood supply line leading to the separation unit for supplying blood to be processed, and a return line leading away from the separation unit for supplying the concentrated cell fraction, wherein the blood supply line includes a first section connected to the inlet of the blood collecting tank and a second section connected to the outlet of the blood collecting tank, and wherein the filter means is arranged in the blood collecting tank; and
   a centrifuge unit, the separation unit of the autotransfusion set being rotatably mounted to the centrifuge unit.

2. The device of claim 1 further including means for supplying an anti-coagulant, the means for supplying an anti-coagulant being connected to the blood supply line of the tubing system.

3. An autotransfusion set for a device for autologous blood transfusion comprising:
   a separation unit for concentrating a cell fraction;
   a blood collecting tank having an inlet and an outlet;
   a device for generating a vacuum connected to the blood collecting tank;
   a tubing system including a blood supply line leading to the separation unit for supplying blood to be processed, and a blood return line leading away from the separation unit for supplying the concentrated cell fraction, wherein the blood supply line includes a first section connected to the inlet of the blood collecting tank and a second section connected to the outlet of the blood collecting tank; and
   filter means for eliminating at least one of leukocytes and tumor cells, wherein the filter means is arranged in the blood collecting tank.

4. The autotransfusion set of claim 3 further including means for supplying an anti-coagulant, the means for supplying an anti-coagulant being connected to the blood supply line of the tubing system.

5. A method of autologous blood transfusion comprising the steps of:
   collecting a quantity of blood from a patient;
   passing the blood through a blood supply line including a first section connected to an inlet of a blood collecting tank, a second section connected to an outlet of the blood collecting tank, and a filter arranged in the blood collecting tank, wherein the blood is drawn into the blood supply line via a device for generating a vacuum which is connected to the blood collecting tank;
   passing the blood through the filter to eliminate at least one of leukocytes and tumor cells;
   centrifuging the filtered blood in order to concentrate a cell fraction, and returning the concentrated cell fraction to the patient.

6. The method of claim 5 wherein the quantity of blood is treated with an anti-coagulant.

* * * * *